US006777374B2

(12) United States Patent
Sahle-Demessie et al.

(10) Patent No.: US 6,777,374 B2
(45) Date of Patent: Aug. 17, 2004

(54) PROCESS FOR PHOTO-INDUCED SELECTIVE OXIDATION OF ORGANIC CHEMICALS TO ALCOHOLS, KETONES AND ALDEHYDES USING FLAME DEPOSITED NANO-STRUCTURED PHOTOCATALYST

(75) Inventors: Endalkachew Sahle-Demessie, Mason, OH (US); Pratim Biswas, Chesterfield, MO (US); Michale A. Gonzalez, Wyoming, OH (US); Zhong-Min Wang, Cincinnati, OH (US); Subhas K. Sikdar, Blue Ash, OH (US)

(73) Assignee: The United States of America as represented by the Environmental Protection Agency, Washington, DC (US)

(*) Notice: Subject to any disclaimer, the term of this patent is extended or adjusted under 35 U.S.C. 154(b) by 0 days.

(21) Appl. No.: 09/906,810

(22) Filed: Jul. 18, 2001

(65) Prior Publication Data

US 2002/0029955 A1 Mar. 14, 2002

Related U.S. Application Data

(60) Provisional application No. 60/218,828, filed on Jul. 18, 2000.

(51) Int. Cl.[7] .......................... B01J 23/00; C01G 23/00; C01G 23/047; C23C 4/10; C23C 16/40
(52) U.S. Cl. ...................... 502/350; 423/598; 423/610; 423/611; 423/612; 423/613; 427/453; 427/255.19; 427/255.31; 428/620; 428/623; 428/632; 428/660; 428/663; 428/323; 428/457; 428/469; 428/472
(58) Field of Search .................. 502/350; 423/598, 423/610–613; 427/453, 255.19, 255.31; 428/620, 623, 632, 660, 663, 323, 457, 469, 472

(56) References Cited

U.S. PATENT DOCUMENTS

| | | | |
|---|---|---|---|
| 3,781,194 A | | 12/1973 | Julliet et al. ............ 204/162 R |
| 4,152,230 A | | 5/1979 | Edwards et al. ........ 204/158 R |
| 5,540,959 A | * | 7/1996 | Wang ......................... 427/561 |
| 5,604,339 A | | 2/1997 | Tabatabaie-Raissi et al. ....................... 204/157.3 |
| 5,622,750 A | * | 4/1997 | Kilian et al. ............. 427/163.2 |
| 5,744,407 A | | 4/1998 | Tabatabaie-Raissi et al. ........................... 442/121 |
| 5,919,726 A | * | 7/1999 | Hatano et al. .............. 502/227 |
| 6,106,955 A | * | 8/2000 | Ogawa et al. .............. 428/469 |
| 6,254,940 B1 | * | 7/2001 | Pratsinis et al. ........... 427/562 |
| 6,387,844 B1 | * | 5/2002 | Fujishima et al. ......... 502/350 |
| 6,455,108 B1 | * | 9/2002 | Muffoletto et al. ........ 427/446 |
| 6,465,088 B1 | * | 10/2002 | Talpaert et al. .......... 428/307.3 |
| 6,500,350 B1 | * | 12/2002 | Hunt et al. .................. 216/16 |
| 2002/0042449 A1 | * | 4/2002 | Ohmori et al. ............... 516/79 |

* cited by examiner

Primary Examiner—Mark L. Bell
Assistant Examiner—Patricia L. Hailey
(74) Attorney, Agent, or Firm—Browdy & Neimark, P.L.L.C.; Anne Kornbau (57) ABSTRACT

Organic molecules are partially oxidized in that the gas phase on supported and immobilized photocatalysts deposited having a nanostructure. the photocatalysts are semiconductors such as titanium dioxide and are preferentially coated onto a substrate by flame aerosol coating.

10 Claims, 11 Drawing Sheets

PROCESS FOR PHOTO-INDUCED SELECTIVE OXIDATION OF ORGANIC CHEMICALS TO ALCOHOLS, KETONES AND ALDEHYDES USING FLAME DEPOSITED NANO-STRUCTURED PHOTOCATALYST

CROSS-REFERENCE TO RELATED APPLICATIONS

The present application claims priority from provisional application No. 60/218,828, filed Jul. 18, 2000, the entire contents of which are hereby incorporated by reference.

FIELD OF THE INVENTION

The present invention relates to partial oxidation of organic compounds in the gas phase to produce valuable compounds on supported and immobilized photocatalysts which have been deposited using a flame aerosol coating method.

BACKGROUND OF THE INVENTION

The cost of handling, treating and disposing of wastes generated annually in the United States has reached as much as 2.2% of the gross domestic product, and continues to rise. The chemical manufacturing industry generates more than 1.5 billion tons of hazardous waste and 9 billion tons of non-hazardous waste annually. Roughly half of the releases and transfers of chemicals reported through the Toxic Release Inventory and 80–90% of hazardous waste generation reported through the Resource Conservation and Recovery Act (RCRA) are due to chemical manufacturing. Organic chemicals comprise the largest amount of toxic release. Many of these releases can be minimized by using better management of materials and energy, more efficient process control, optimizing process conditions, and recycling and reusing waste and byproducts. However, cleaner products methods can be achieved by adopting "green synthetic" methods.

Oxidation reactions are used in industry for producing aliphatic and aromatic aldehydes, alcohols, ketones and carboxylic acids. Generally, oxidation involves splitting of C—C or C—H bonds with concomitant formation of C—O bonds. For example, the partial oxidation of hydrocarbons by molecular oxygen to form oxygenates, which are further used as building blocks in manufacturing plastic and synthetic fibers, is an important process in the chemical industry. Oxidation reactions are usually catalyzed and are carried out in liquid or gas phase. The current processes are energy intensive, have low conversion coefficients, and generate environmentally hazardous waste and byproducts.

Current processes for producing these highly desired oxygenates require stringent operating conditions such as high temperatures and pressure, strong acids, free radicals (halogenated starting materials) and corrosive oxidants. Although these processes are currently being used, they have low energy efficiencies and generate environmentally hazardous waste and byproducts. One major reason selectivities are low is that the desired products, such as carbonyls and alcohols, are more easily oxidizable by oxygen than is the parent hydrocarbon. Over-oxidation must be minimized by maintaining conversions low, which is a serious disadvantage from the viewpoint of chemical processing and economics. Therefore, a major challenge is to find reaction pathways that produce the primary product with high selectivity and at high conversion rates for the hydrocarbons.

Most oxidations are highly exothermic and may generate high localized temperatures and hot spots on the catalyst surfaces, decreasing the service lifetime of the catalyst and resulting in over oxidation of desired products. Over oxidation can be minimized only by keeping conversions low. Therefore, a major challenge in this field is to find a reaction pathway that affords the primary product with high selectivity and a high conversion rate of the hydrocarbons. There is a strong research effort underway to meet this challenge. Unfortunately, several commonly used catalysts for oxidation reactions are toxic heavy metals such as chromium and vanadium, or strong acids such as sulfuric acid or nitric acid. Pollution is inevitable in loading, recovering, and regeneration of these catalysts. A cleaner alternative is needed.

Photocatalytic or photoactivated reactions are applicable to a wide range of valuable industrial processes, including organic synthesis, photodestruction of toxic compounds, and purification of drinking water. The anatase form of $TiO_2$ has been the most extensively used in photocatalytic reactions because of its high activity and chemical stability. For example, the anatase phase of titania can be used as a photocatalyst for several problems of environmental interest, as a catalyst for sulfur removal, for toxic metals capture, and as an additive in cosmetics because of its effective sunscreen properties.

The electronic structure of titania is characterized by a filled valance band and an empty conduction band. When a photon with energy exceeding the band gap energy is incident, an electron is readily excited to the conduction band, leaving a hole in the valence band. If surrounding and surface conditions are correct, the excited electron and hole pair can participate in reduction-oxidation reactions. The quantum efficiency of the semiconductor photocatalyst depends on the recombination lifetime of holes and electrons, and the rate of interfacial charge transfer. Therefore, crystal structure, grain size, and attendant surface morphologies can affect quantum efficiencies.

Recently, titania has been used in an atmospheric pressure process for coating steel substrates to provide for stainless and corrosion resistance characteristics. Several researchers have been studying different applications for titania films, relying on its self-cleaning and superhydrophilic properties. The feasability of this technology on a commercial scale has also been demonstrated by the implementation of numerous small-scale applications for treating contaminated air and water streams.

Photocatalytic oxidation of many organic molecules, including saturated hydrocarbons, by optically excited semiconductor oxides is thermodynamically feasible in the presence of oxygen at room temperature. UV light-assisted oxidation has been shown to be promising for oxidizing cyclohexane and epoxidizing small olefins. Selectivities different from those obtained by other oxidation routes have been reported, illustrating the potential of the method for syntheses, provided that that the expected product can be obtained with an acceptable yield.

The rate of photooxidation is affected by the solvent type, colloidal preparation, the oxygen concentration, catalyst surface area, and light intensity. Aromatic aldehydes have been synthesized by oxidating the methyl groups of toluene and derivatives by routes which can also yield the corresponding alcohols and carboxylic acids. Various factors controlling the yield and specificity of the reaction products have been investigated, as the photophysics of the various excited states reactions occurring at the titanium dioxide/non-aqueous solution interfaces. Such additional thermodynamic control or redox chemistry for systems containing the semiconductor catalysts has been previously ascribed to differences in that the adsorption of the various oxidizable species to be adsorbed on semiconductor surfaces.

Most studies related to synthesizing compounds using titania catalysts have been performed in the liquid phase. Sahle-Demiessie et al., in Ind. Eng. Chem. Res. 1999, 38, 3276–3284, describe the activation and oxygenation of hydrocarbons in the gas phase by irradiating supported titania films with ultraviolet irradiation. The oxidation in the gas phase eliminates an additional separation step, as the catalyst is supported. Product adsorption can also be minimized by using slightly elevated temperatures. Furthermore, operating conditions such as feed rates, humidity, mixing conditions, and residence times can be readily controlled. One concern, especially in gas-phase reactors for complete oxidation to carbon dioxide, has been the formation of byproducts that lead to catalyst deactivation. For wide-scale applicability and commercialization of this technology, it is essential to develop reactors with well-controlled thin films that are not readily deactivated.

Designing the photocatalytic reactor with films of controlled characteristics is thus an important consideration for practical application. Several different methodologies have been used to produce titania powders and films, including wet processes, sol-gel processes, and gas phase processes. Gas phase coating processes have the advantage that no toxic liquid waste byproducts are produced, and, moreover, these properties can be controlled so as to obtain the desired properties. Various dry coating methods such as ion plating, sputtering, plasma chemical vapor deposition, chemical vapor deposition, and physical vapor deposition have been developed for the electronics industry. However, most of these processes are low pressure processes and are either not feasible or are too expensive for coating larger areas. Also, the film composition and other properties cannot readily be varied using these coating methods.

Yang et al. have developed atmospheric pressure coating methods for applying ceramic coating onto steel and quartz substrates, and have obtained superior adhesion and corrosion resistance properties. Using flame aerosol coating, films of 5 nm to 1 micron were deposited onto stainless steel and silica substrates.

Tabatabaie-Raissi et al., in U.S. Pat. Nos. 5,604,339 and 5,744,407, describe methods for destroying toxic volatile air-borne toxins using a chemical membrane based on titania which acts as a photocatalyst for inhibiting emissions of harmful volatile organic compounds. A suspension of titania in water is coated onto a substrate to produce such a membrane.

Edwards et al., in U.S. Pat. No. 4,152,230, disclose a photochemically initiated oxidation process for organic chemicals by conducting the reaction in the presence of a compound of a multiple valent metal, especially copper, to trap the photochemically produced radicals. In this case the metal must possess a reduction potential which is not so high that the compound would oxidize the organic substrate on its own without the initial hydrogen abstraction process effected by the photochemically activated species. Among the metals that can be used are copper, iron, cobalt, manganese, chromium, and vanadium.

Juillet et al., in U.S. Pat. No. 3,781,194, disclose a process for photocatalytic oxidation of hydrocarbons into aldehydes and ketones. Among the catalysts that can be used for this process are titania, zirconia, and magnesia.

SUMMARY OF THE INVENTION

It is an object of the present invention to overcome the aforesaid deficiencies in that the prior art.

It is another object of the present invention to synthesize high-value organic compounds using photocatalytic oxidation with semiconductor material.

It is a further object of the present invention to provide a process for partially oxidizing organic chemicals to alcohols, ketones, and aldehydes, using flame deposited nanostructured photocatalysts.

It is another object of the present invention to activate and oxidize hydrocarbons using light energy and a specially prepared catalyst.

It is yet another object of the present invention to produce industrially useful products at high selectivity while producing minimal byproducts and pollutants.

According to the present invention, high value organic compounds are synthesized using photocatalytic oxidation with a flame-deposited semiconductor material such as titanium dioxide. The process of the present invention can be applied to a variety of hydrocarbons which can be oxygenated in both liquid and gas phase using ultraviolet light and a semiconductor under mild conditions.

According to the present invention, gas phase photocatalytic oxidation reactions of hydrocarbons are effected by flowing a known mixture of heated humid air along with the organic vapor through a reactor, preferably an annular reactor. The inner wall of the reactor is coated with a semiconductor film which had been deposited using a flame aerosol method. The efficacy with which the photoreactor operates is influenced by the oxygen concentration, the light illumination, the properties of the photocatalytic coating, and the conditions within the fluid phase affecting contact to the substrate to the titania surface.

In particular, air and substrate are reacted at ambient conditions in a gas phase photocatalytic reactor that uses ultraviolet light, preferably of solar origin, and a specifically prepared semiconductor catalyst, such as titanium dioxide.

The present invention provides clean production technology by selectively producing partial oxygenates and producing less by-products and pollutants than conventional oxidation reactions. The present invention incorporates the idea of "atom economy" by direct oxygenation of hydrocarbons without using multiple stages or loss of atoms.

DETAILED DESCRIPTION OF THE INVENTION

The present invention relates to an effective and cleaner process for oxidizing organic compounds to useful products using ultraviolet irradiation and a semiconductor phtocatalyst.

Semiconductors are solids that have electrical conductivities between those of conductors and those of insulators. Semiconductors are characterized by two separate energy bands: a low-energy valence band and a high-energy conduction band. The energy separation between the valence and conduction bands is called band gap and consists of energy levels in which electrons cannot reside.

The term "semiconductor" encompasses a large number of materials, most of which crystallize in either the zincblende (cubic), wurtzite (hexagonal), or rock salt (cubic) crystal structures. The most common examples of these compounds are titanium dioxide, silicon dioxide, gallium arsenide, cadmium sulfide, and lead sulfide. Other zincblende semiconductors are $ZnSiP_2$ and $Ga_2Se_3$. Other semiconductors include AnMgSe, HgCdTe, CdTe and HgTe.

Semiconductors such as titanium dioxide are photoconductive when illuminated by photons having an energy level that exceeds its band-gap energy, in the case of $TiO_2$, 3.2 eV. The UV spectrum is arbitrarily divided into three band ranges: UV-A (315–400 nm), UV-B (280–315 nm), and UV-C (100–280 nm). UV-A radiation, which is also referred to as long-wave radiation or black light, is the preferred range for the process of the present invention, generally with peak light emission at 370 nm. For titanium dioxide, the photon energy required to overcome the band gap energy and to excite an electron from the valence band to the conduction band can be provided by light having a wavelength shorter than 387 nm. Different semiconductors have different energy requirements to excite an electron from the valence band to the conduction band, and thus the wavelength of light used will vary with the particular semiconductor used.

Light energy can be used to excite electrons from the valence band into the conduction band. When an electron in the valence band absorbs a photon, the absorption of the photon increases the energy of the electron and enables the electron to move into one of the unoccupied energy levels of the conduction band, creating a "hole" in the valence band and excess electrons in the conduction band. The holes react with water to form .OH, and the electrons in the conduction band reacts with oxygen to form superoxide ions, $O_2$. The superoxide ions react with water to provide additional .OH and oxygen. These free radicals are responsible for the oxidation process.

Various hydrocarbons were partially oxygenated in both aqueous and gaseous phase reactors using ultraviolet light and titanium dioxide at mild conditions. The conversions and selectivities obtained for the partial oxidation of hydrocarbons have been comparable to those achieved with conventional methods.

Gas phase oxidations have higher reaction rates, eliminate the separation stages necessary with liquid phase reactions, and exhibit minimum product adsorption to the catalyst, since the temperatures are slightly higher for gas phase oxidation than liquid phase oxidation. Furthermore, operating conditions such as feed rates, humidity, mixing conditions, and residence time can be more readily controlled. For wide-scale applicability and commercialization of this technology, it is essential to develop reactors with controlled thin films that are not readily deactivated.

Thin films of titania or other semiconductors are preferred photocatalysts for organic degradation. This type of catalyst avoids the separation of suspended powders and provides the potential for scaling up. In addition, thin-film catalyst can be connected to an external power source to reduce the recombination of UV-activated electrons and holes, thereby increasing quantum efficiency. The immobilization of a semiconductor on a solid carrier as a thin film catalyst introduces several mechanisms not normally found in conventional semiconductor slurry processes.

The aerosol deposition method of the present invention permits deposition of homogeneous thin films following the microscopic structure of the substrate, whereas other methods often have problems with shading. Once the film is coated, the growth per dip cycle is constant and reproducible during the process. Designing the photocatalytic reactor with films of controlled characteristics is thus an important consideration for practical applications. Gas-phase coating processes have the advantage that no toxic liquid waste byproducts are produced. Moreover, these processes can be controlled so as to obtain desired properties of the coating materials. Flame aerosol coating methods have several advantages over other coating methods. One can engineer the coating process to control the particle size, film thickness and morphology using a single step process with minimum waste generation. It has already been reported that with unsupported photocatalyst, the kinetics are limited by adsorption of organic substrate, while for supported photocatalyst the kinetics are diffusion-limited. However, these comparisons were not done on catalysts having similar surface area and porosity. Flame aerosol methods can produce a highly porous semiconductor film that can be as efficient as nonsupported photocatalysts. The photocatalytic activity of aerogels and aerosols is much better than commercially available semiconductors.

There are many advantages to performing oxidation in the gaseous phase. These include the ability to eliminate a separation step, since the catalyst is supported, as well as the inhibition of product adsorption on the catalyst that directly results from the use of elevated temperatures (100–175° C.) within the reactor assembly. Other benefits include the ability to control feed rates, humidity of the air stream, mixing conditions, temperatures of the feed, mixing, reactor, and exit port, and contact times of the catalyst bed. Initial reactions performed with a gas phase reactor using anatase titania supported on a porous fiber surface of the oxidation of cyclohexane demonstrate the production of cyclohexanol and cyclohexanone, the major products.

Figure 1:
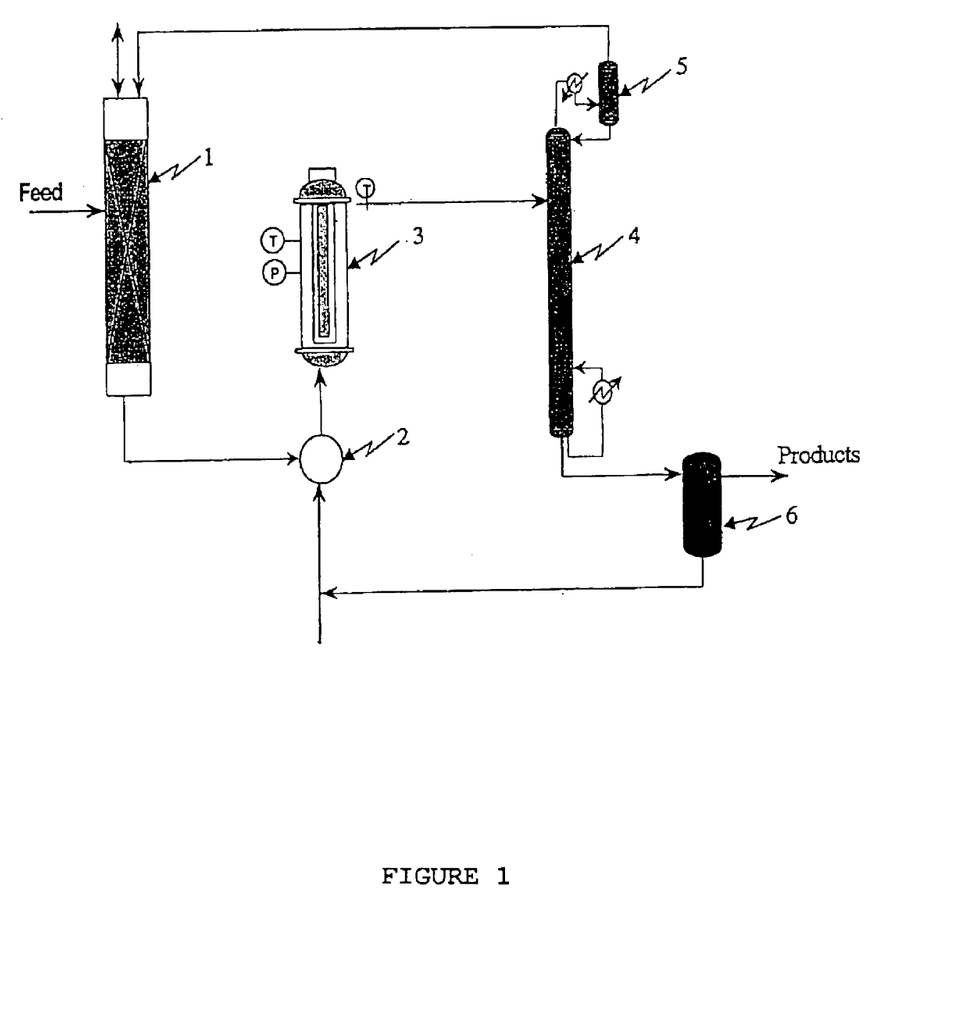
FIG. 1 is a schematic illustration of continuous processing equipment that can be used in performing the process of the present invention.

The system shown in FIG. 1 has been used to coat surfaces using a flame aerosol reactor and has been used to successfully coat stainless steel and quartz substrate with varying thicknesses of anatase or rutile titania, from a few nanometers to micrometers. The system consists of a diffusion flame burner or premixed flame burner with a precursor feed system consisting of an atomizer or bubbler. Coating precursors include organometallic compounds, including isopropoxides, nitrates ($Fe(NO_3)_3$@$9H_2O$), carbonyls, HMDs, etc. Other precursors include titanium tetrachloride, tin chloride, silicon tetrachloride, etc. The titanium precursors, titanium isopropoxide, was entrained in the gas stream and introduced into the flame of methane-air/oxygen. The flow rates were precisely controlled to obtain different processing conditions of temperature (750 EK to 3000 EK), residence time (1 ms to 10 second), and feed rates.

Figure 10A:
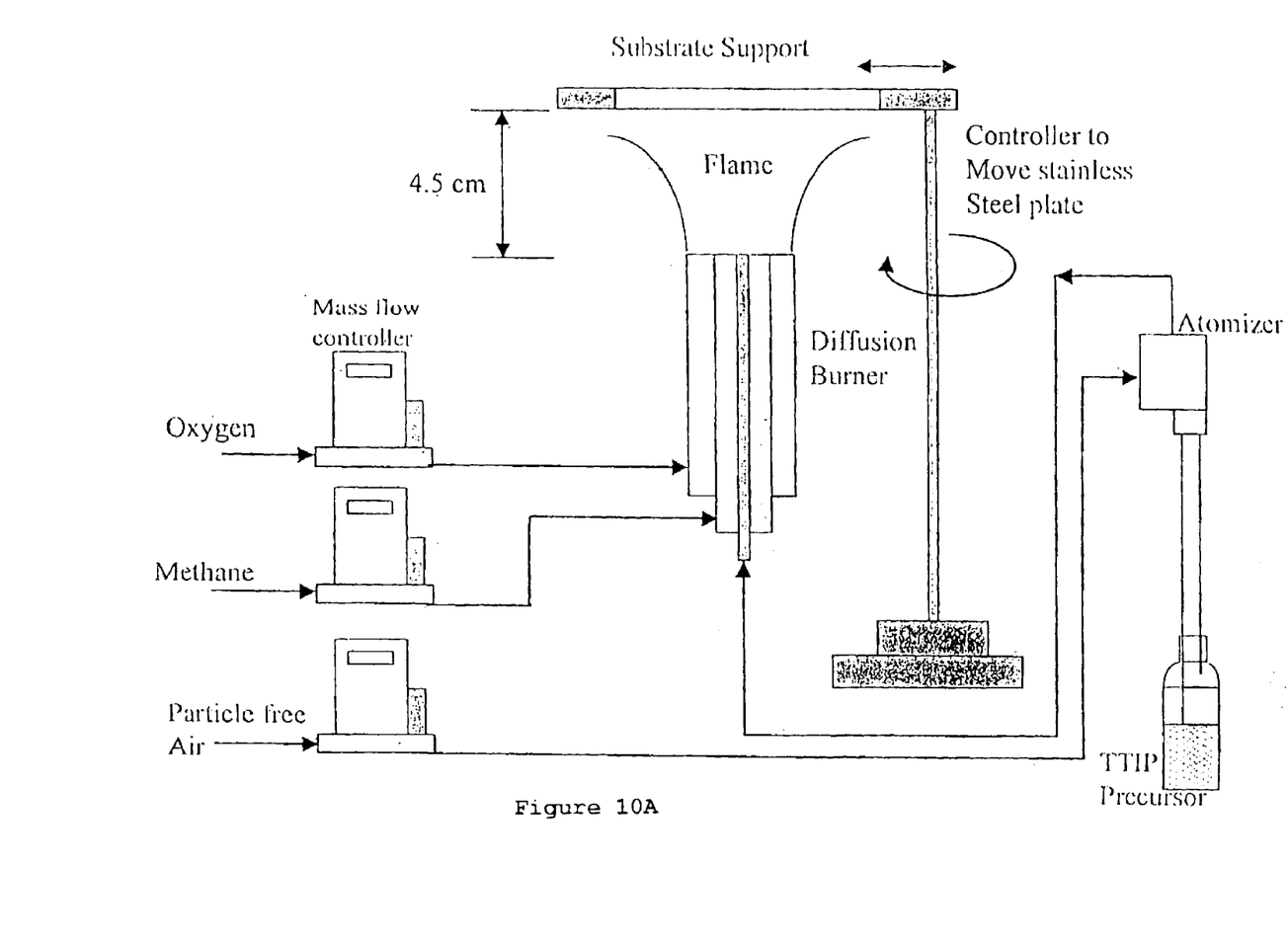
FIG. 10A illustrates a system in which the precursor aerosol is impinged onto a heated substrate.
Figure 10B:
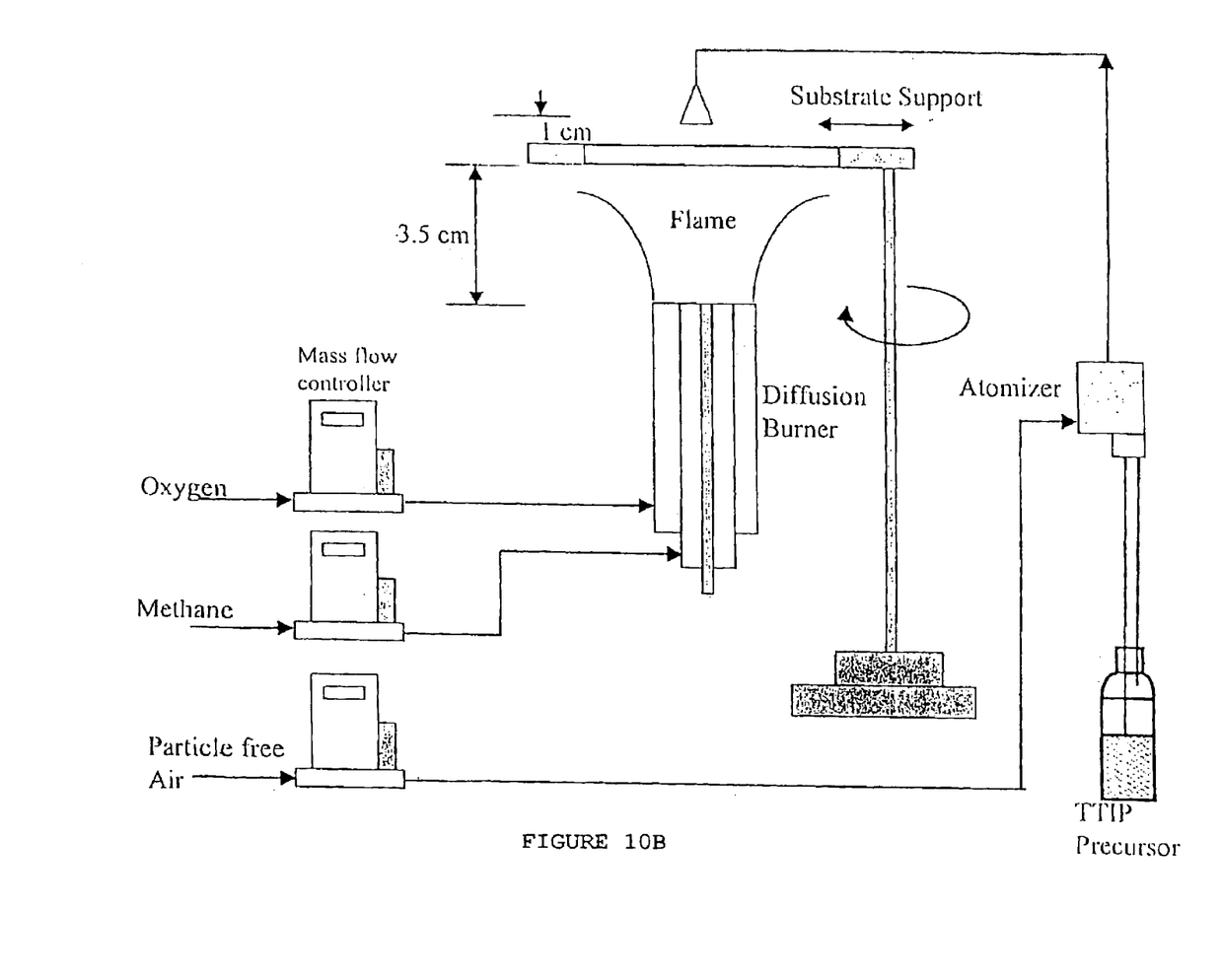
FIG. 10B illustrates a system in which fuel and pre-cursor are fed through a burner.

Two different coating strategies were adapted, including impinging a precursor aerosol onto the heated substrate as shown in FIG. 10A, and co-feeding the precursor and the fuel through the burner, as shown in FIG. 10B. The operating conditions are listed in Table 1, and the number of passes was controlled to vary the thickness of the resultant titania films. The substrates which can be coated with the semiconductor include silica fibers, silica, quartz, stainless steel, steel, aluminum and other ceramic fibers. The operating conditions for the flame coating methods are listed in Table 1, and the number of passes was controlled to vary the thickness of the resultant titania films. As high temperatures were used during application of the coating, no additional steps were necessary, and well adhered films were readily obtained in a single step. This cycle was repeated until the desired layer thickness was obtained. Although the high temperature used in the aerosol route result primarily in the anatase phase because of quenching effects, the rutile phase can also be achieved by adjusting the flame and flow conditions.

TABLE 1

The operating conditions for the flame coating method

Figure 2:
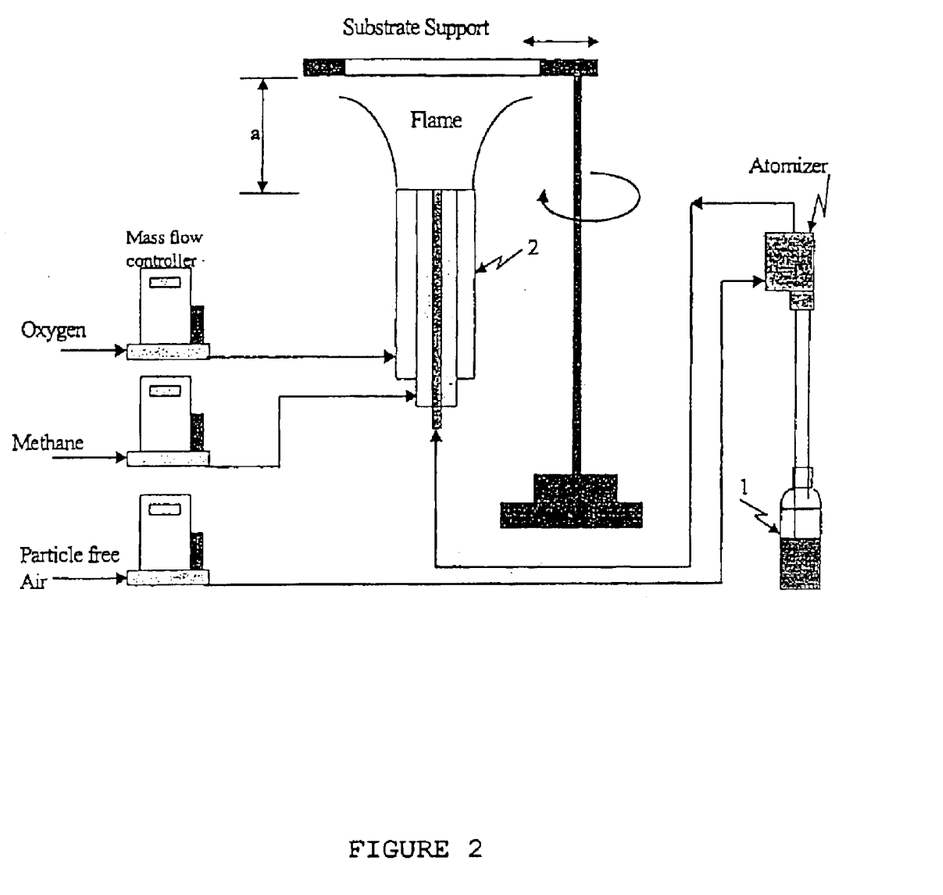
FIG. 2 is a schematic illustration of flame aerosol coating system that can be used to make semiconductor films by flame aerosol.
Figure 3:
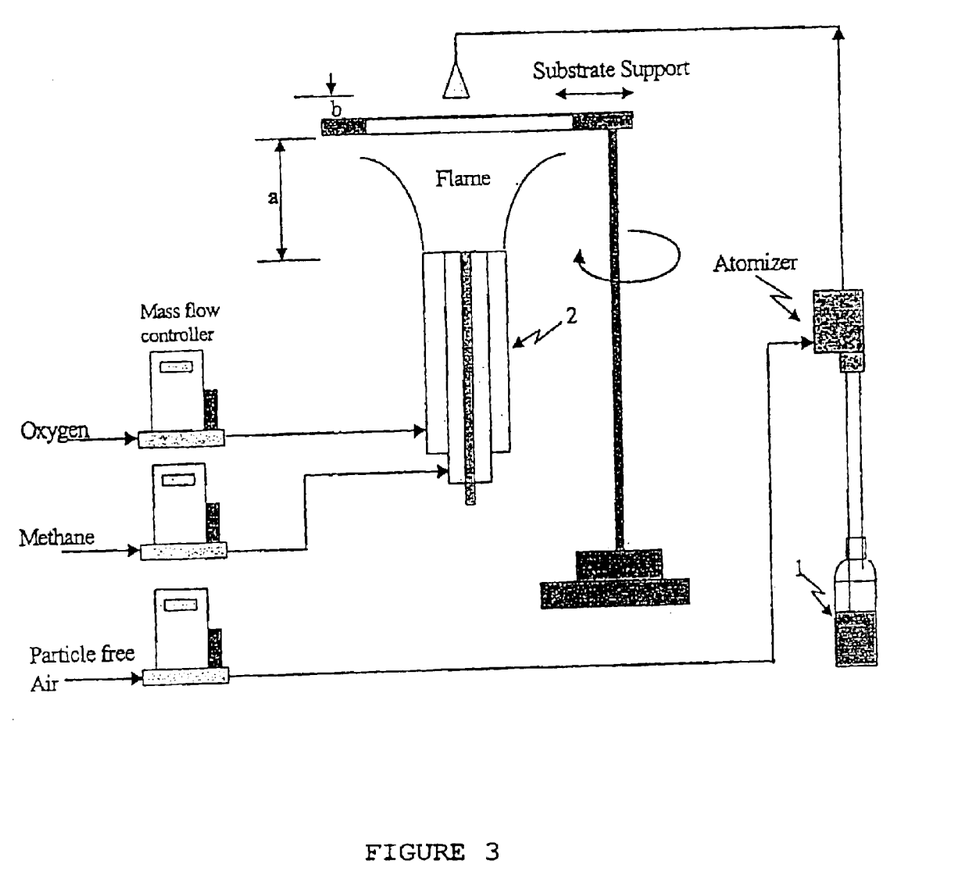
FIG. 3 is a schematic illustration of the flame aerosol coating system that can be used to make semiconductor films.

| Case Number | Flow Rate (L/min) | | | Coating | |
|---|---|---|---|---|---|
| | Methane | Oxygen | Air Through TTIP Bubbler | Configuration | Number of Coating Scan |
| FIG. 2 | 0.5 | 2.1 | 3.83 | Opposite | 10 |
| FIG. 2 | 0.5 | 2.1 | 3.83 | Opposite | 4 |
| FIG. 3 | 0.5 | 3.0 | 3.83 | Through Flame | 4 |

TABLE 2

Experimental Conditions for the Partial Photo-Oxidation Process

| Parameter | Value |
|---|---|
| Air flow rate, L/min | 1.5 |
| Relative humidity, % | 90 |
| Additional oxygen flow, L/mm | 0.5 |
| Substrate flow rate, ml/min | 10 |
| Oxygen/cyclohexane mole ratio | 22 |
| Residence time, sec | 8 |
| Temperature (° C.) | 150 |
| Irradiated surface area (cm$^2$) | 243 |
| Irradiance of TiO$_2$ surface (mW/cm$^2$) | 27 |

Two techniques were used to characterize the deposited film. An X-ray diffraction method was used to identify the phase compositions and establish the crystal structure. Scanning electron microscopy was used to establish real space structures, deposited film thickness, particle sizes and morphologies. Titanium coated stainless steel was cut with aviation shears into sections of approximately 250 cm$^2$.

Photoactivation of Hydrocarbons using Immobilized Semiconductors

Titania films provide a fixed environment for the reactivity of a wide range of organic compounds and a means for generating light-induced redox activity. Light-induced titania film photooxidizes hydrocarbons. This oxidation either accomplishes either a specific, selective oxidation or a complete degradation of an organic compound. Much work has been done using band-gap irradiation of semiconductor particles for novel redox reactions of organic compounds. the possibility of using semiconductor photocatalysts to induce selective, synthetically useful redox transformations in specific organic compounds has been increasingly more attractive.

Figure 7:
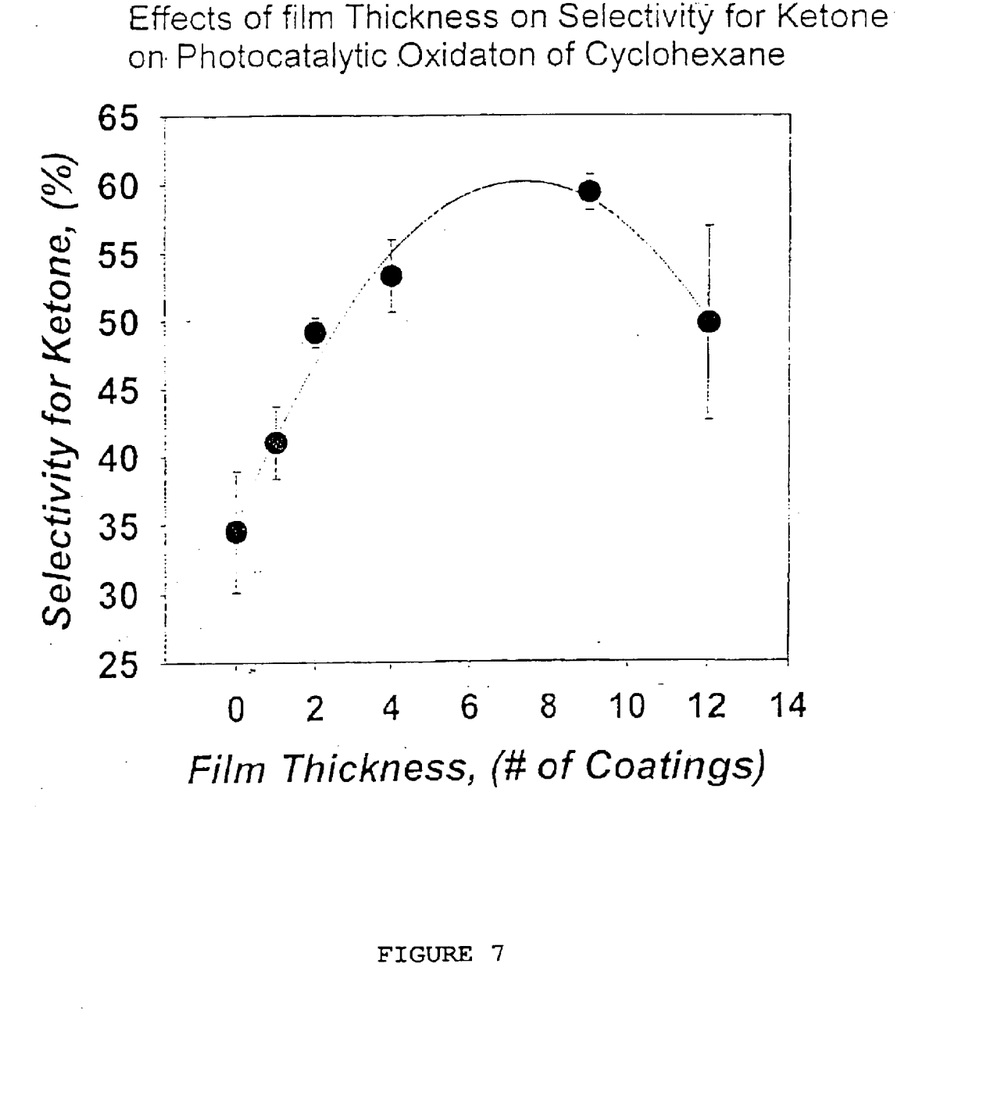
FIG. 7 shows the effects of film thickness of selectivity for ketones.

Gas phase photo-induced catalytic oxidation of hydrocarbons was performed by flowing a known mixture of heated humid air (i.e, relative humidity above 50%) with the organic vapor through an annular reactor, 10 cm, outer diameter, 5.2 cm inner diameter, 30 cm length. The process flow diagram is shown in FIG. 7 for a continuous reaction system that can be used for performing gas phase photo-activated catalytic oxidation of organic compounds. Stainless steel foil coated with a titania film was inserted into the reactor. The coated film area that was irradiated was about 243 cm$^2$ for all the experiments. The light source was a 450 W medium pressure mercury vapor quartz lamp (Hanovia) and was placed inside a quartz cooling jacket that was immersed in the vapor phase reactor. The intensity of the UV light was measured using a photometer (International Light, Model IL 1400).

Liquid organic feed (HPLC grade from Aldrich) was pumped using a metering pump at a rate of 10 ml/hr. The cyclohexane was heated and vaporized before it was fed to a static mixer. Two mass flow controllers (Kobold MFC-5108, Pittsburgh, Pa.) were used to set the desired flow of air and supplementary oxygen at the rates of 1.5 and 0.5 L/minute, respectively. The feed air flowed through two air bubbling humidifiers that were kept at 60° C. Gases were heated to 90° C. before being distributed to the static mixer (Omega FM 8400). All the gases and the organic vapor were premixed in the static mixer that was maintained at 120° C. The experimental conditions used are listed in Table 2. The intensity of UN light irradiation was measured using a photometer (International Light, Model IL 1400).

The exit stream from the reactor was passed through a series of three condensers maintained at −5° C. to capture the products before venting out to the fume hood. The system was allowed to reach thermal equilibrium for about an hour with the air flowing and the lamp turned on. When steady-state conditions were achieved, the cyclohexane feed was introduced. The average gas flow rate of 2 L/minute used resulted in a minimal mass-transfer resistance, as verified by calculations.

Chemical Analysis

After the cyclohexane feed was introduced, the reactor exit gas stream was sampled every 30 minutes and the condensed liquid product was collected and analyzed at hourly intervals. Organic compounds were analyzed using a gas chromatography (Hewlett Packard 6890) with a flame ionization (FID). Separation of products was achieved with a HP-capillary column (HP-5, 30 m×0.25 mm column) with split/splitless heated injection port. Permanent gases, primarily carbon dioxide and oxygen, were analyzed using a J.W. Scientific Gas-Pro (30 m×0.32 mm) column and a thermal conductivity detector (TCD). A gas sampling loop (0.2 ml) allowed capture of aliquots of either the reactant feed or the product stream. Each gas was delivered to the gas chromatograph via an automatic valve actuator system. A minimum of two injections were performed for each gas phase sample. Liquid product samples were analyzed using the above-mentioned GC/FID system. The sample volume injected was 1.0 mL, and at least two injections were made for each sample. Products were identified using a Hewlett-Packard Gas Chromatograph with a low bleed column (HP-SMS, 30 m×0.25 mm) equipped with a Mass Selective Detector (HP 6890/5973). This instrument conducts both qualitative and quantitative determinations.

Results and Discussion

Irradiation of titanium dioxide with UV light having photons of energy higher than the band gap energy ($E_g$) leads to the formation of a pair of conduction band electrons ($e^-_{CB}$) and valency band holes ($h^+_{VB}$):

The charge carriers thus formed can recombine or be trapped by a defect site at the particle surface and subsurface via interfacial electron transfer with adsorbed electron donors ($Red_2$ and acceptors ($Ox_1$)ads. The presence of molecular oxygen and moisture is essential for the process.

Partial Oxidation

Photoactivated immobilized semiconductor surfaces provide an environment where light-induced redox reaction can take place, resulting in partial to complete oxidation of organic compounds. The major form of the partial oxidation is attributed to heterogeneous photocatalysis and a smaller amount of photolysis, i.e., photochemical reaction due to absorption of photons.

A mechanism for oxidation of cyclohexane is provided via two steps. The first step involves the abstraction of a hydrogen atom from the substrate cyclohexane R by either a TiO or Ti—OH species, forming a R*, Ti—OH*, and/or Ti—OH$_2$* species, respectively. The second step involves radical recombination, which occurs between the newly formed R* species and OH* and HO2* species generated by the reaction of water with the photo generated holes on the titania surface, leading to the production of the hydroxylated cyclohexanone (ROH) product. The formation of cyclohexanone occurs from further oxidation of cyclohexanol on the catalyst. This mechanism is consistent with the mechanism proposed in the literature:

Of particular interest is the selective oxidation of hydrocarbons and aromatics to the corresponding oxygenates where semiconductors function as the photocatalyst. The preferred semiconductor, titanium dioxide, is biologically and chemically inert, stable with respect to photo corrosion and chemical corrosion, and an inexpensive catalyst. When the anatase form of titania is illuminated by UV light with wavelengths below 390 nm, absorption of the light within the solid allows excitation of valence band electrons into the conduction band, leaving behind holes. The photo generated holes are believed to have an oxidation potential of about 2.6V, therefore possessing considerable oxidizing capability. If these electrons and holes can reach the surface of the catalyst, a reaction between species at the particle-solution interface occurs. The species to be oxidized is believed to adsorb on the surface of the particles and to intercept the energetically favorable and rapid process of electron-hole recombination. Therefore, photochemical reactions at particle/solution interfaces are controlled by both relative redox energies and adsorption characteristics. Selectivities different from those obtained by other oxidation means have been obtained with an acceptable quantum yield, demonstrating the potential of this method for syntheses.

The present invention is an improvement over previous photooxidation using semiconductor photocatalysts because the semiconductor catalyst is nanostructured at optimized process conditions, providing high conversions and selectivities with little or no detectable over oxidation. Results obtained from a gas phase reactor at 150° C. and with contact time of 8 seconds are shown in Table 2.

Effects of Film Thickness

Figure 8:
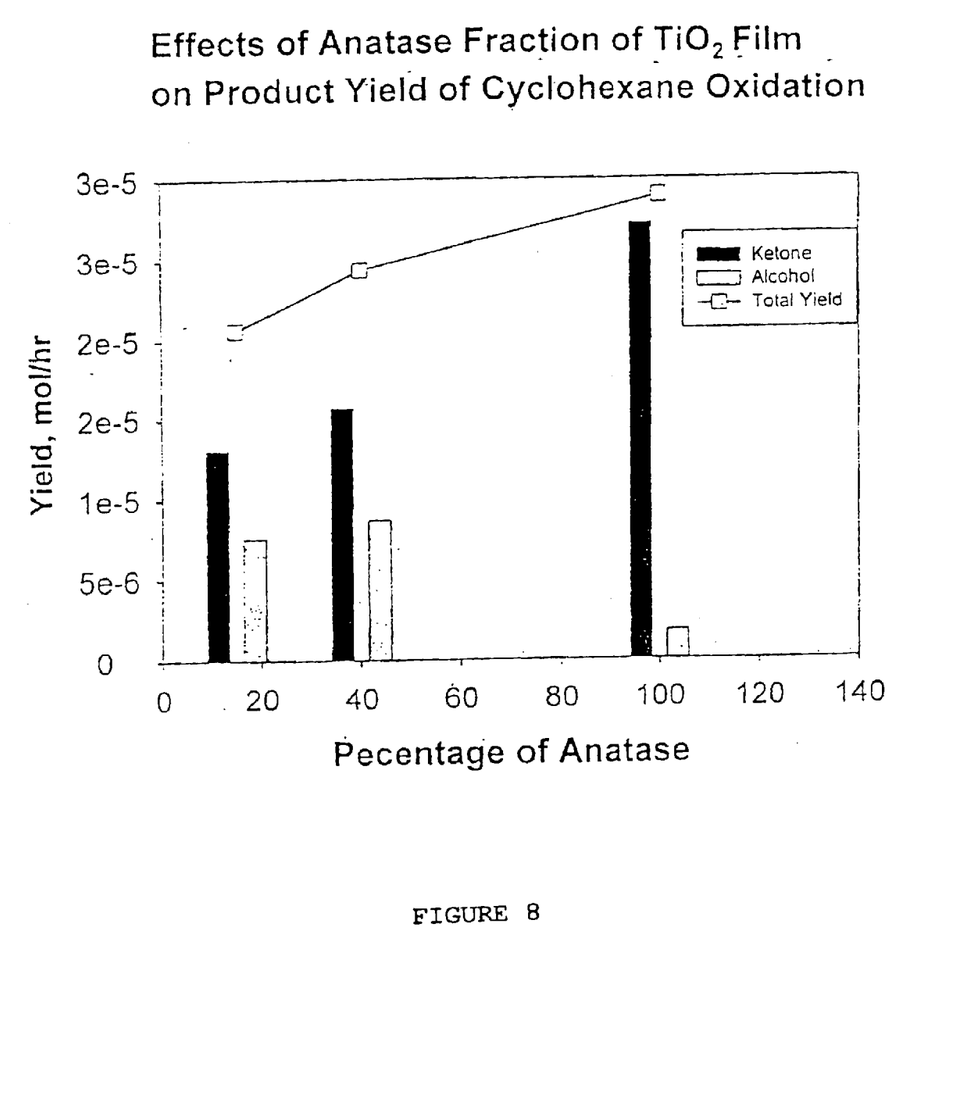
FIG. 8 shows the effect of the anatase fraction of titanium dioxide film on yield of cyclohexane oxidation.

One of the properties of nano-structured films that can easily be changed is the thickness of the film. The effect of the thickness of aerosol coated film on the total yield of the partial oxidation of cyclohexane is shown in FIG. 7. A single layer film coated using the aerosol method was measured using a scanning electron microscope to be about 50 nm. The number of coatings is approximately correlated with the film thickness by measuring films of four, eight and twelve layers. At small thicknesses, the amount of cyclohexane conversion or product formation increased with an increase in film thickness. This increases in yield of oxygenates can be attributed to an increase in the amount of catalyst available to be activated by UV for the photoreaction. As the film thickness increased to about 400 nm, the amount of yield of alcohol and ketone, and total yield of oxygenates, reached maximum of $5 \times 10^{-5}$ mol/hr, as shown in FIG. 8. The selectivity for ketone reached a maximum of 66% for the same thickness range. For thicknesses between 400 and 800 nm, the increase in film thickness simply serves as an inert support and did not provide additional photocatalytic power. As the thickness increased to 0.8 to 1.5 micron, the product yield and selectivity for ketone begins to decrease. There are two explanations given for this. First, a slow diffusion limits the number of molecules reaching the interior of the catalyst. For films having porous and open structures, little changes were observed when more layers of catalyst were used. Second, as the film thickness increases, the number of surface active sites increases. However, light penetration into the film decreases because of the limiting intensity of light reaching the interior of the film and the light-scattering of the catalyst. This decrease in activity has been observed in several other studies. Anderson et al., *J. Environ. Eng.* 122, pp. 217–221, 1996 and *J. Photochem. Photobiol. A* 94, pp. 221–229, 1996, used titania coated glass slides and stainless steel plates to degrade formic acid in aqueous solution. They found the amount of acid degraded maximum for sol-gel coated titanium dioxide at 7 layers. Light penetration depth would vary not only for the film thickness but also with particle size and porosity, with a maximum depth less than 2 microns. Termakone et al., *Water Res.* 31, pp. 1901–1912, 1997, reported the degradation of carbofuran by a thin-film titanium dioxide catalyst reached a maximum at 20 coating, about 6 microns.

Effect of Particle Crystal Structure

The effect of the crystallographic structure of titanium dioxide on photolysis efficiency has been studied by many researchers. Titanium dioxide in the anatase form appears to be the most photo active and the most practical of the photocatalysts for wide applications. Many researchers claim that rutile is a catalytically inactive or a much less active form of titanium dioxide, while other find that rutile titanium dioxide has a selectivity for certain substrates. Rutile titanium dioxide was shown to be a significantly better catalyst for oxidation of CAN$^-$ than the anatase form.

In most previous studies variation of anatase-to-rutile content of titanium dioxide was achieved either by using different titanium dioxide preparation methods or by sintering commercially available titanium dioxide at temperatures between 600 and 900° C. for a variable period of time. This kind of thermal anatase-to-rutile transformation results in a significant reduction in specific surface area. The influence of these two parameters, specific surface area and crystal structure, must be decoupled to understand their influence correctly.

Flame aerosol deposition permits good control of particle size, morphology, and crystal structure by controlling the conditions of the flame and collection surface. The titanium dioxide film deposited does not require a thermal treatment such as a sintering process to achieve crystallinity.

Figure 9:
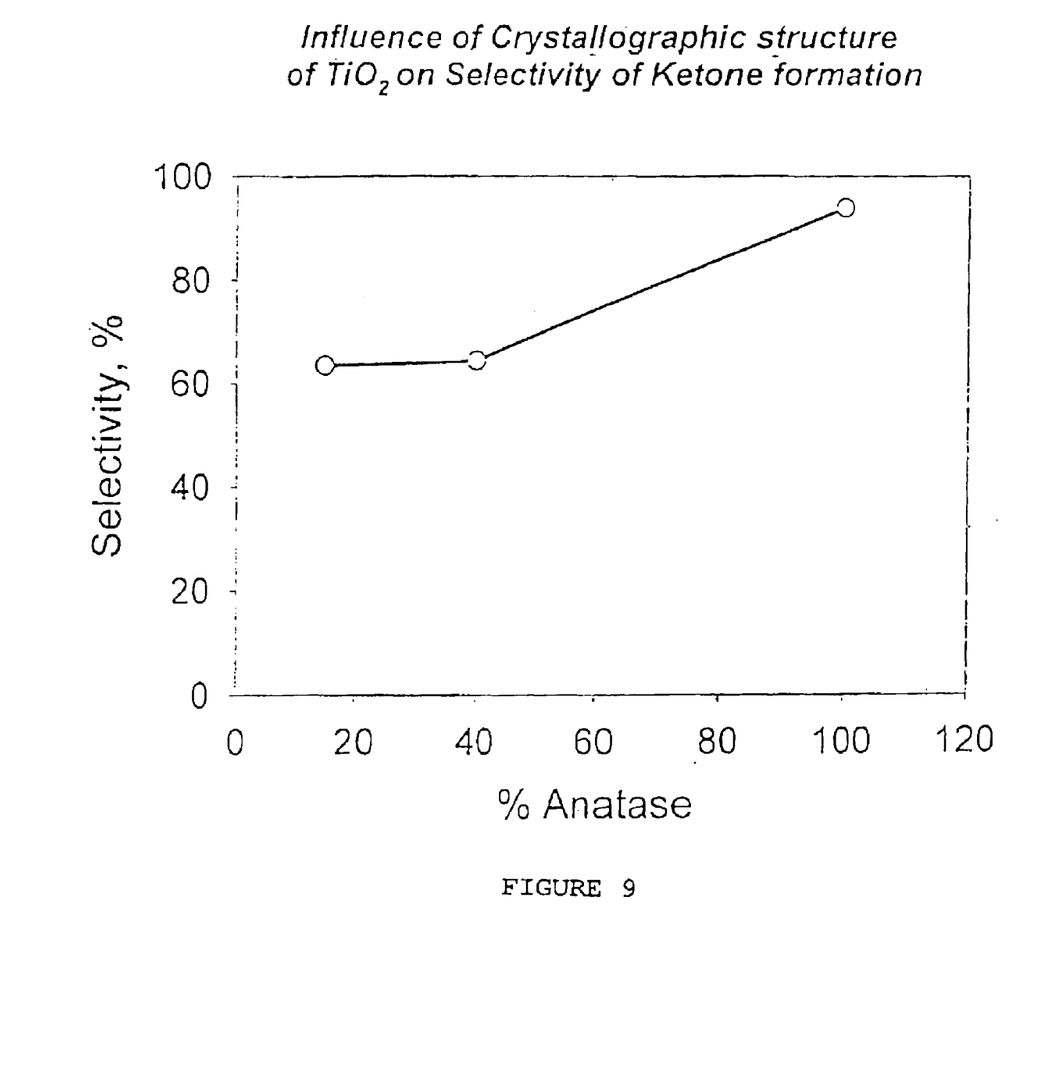
FIG. 9 shows the influence of the crystallographic structure of titanium dioxide on selectivity of ketone formation.

Results of the influence of crystallographic structure of titanium dioxide on the yield of cyclohexanol and cyclohexanone and selectivity for the ketone are shown in FIGS. 8 and 9. Both the yield and selectivity in the partial oxidation of cyclohexane using pure anatase were about 40% higher than those observed for 20% anatase and 80% rutile. Selectivity for the ketone increased linearly with the increase in the anatase fraction for 20 to 95%, indicating that higher activity favors the successive reactions. The difference in the performance of the anatase and rutile crystal structures of titanium dioxide may be explained using two factors. Using diffuse reflectance spectra, which is the ratio of the adsorption and scattering coefficients, the light-adsorption capacity of the anatase form was measured to be in the near-UV region, approximately 390 nm, and was significantly higher than that of the rutile form, which has adsorption capacity shifted to the higher wavelength of 410 nm. The difference in the band gap energy, 3.2 eV for anatase compared to 3.0 eV for the rutile form, could also account for the higher performance of the anatase structure.

Effects of Particle Morphology

Flame aerosol deposition was used to deposit two different particle morphologies: a thin uniform film and a porous open structure. The deposited particles were loosely-packed spherical particles of average diameter of about 150–400 nm. The very high surface area and pore volume made nanostructured aerogels more active and selective for certain reactions.

The following examples are presented for the purpose of further illustration and explaining the present invention and are not to be taken as limiting in any regards.

EXAMPLE 1

In FIG. 1, a process flow diagram is shown for a continuous reaction system 3 that can be used in performing gas phase photo-activated, catalytic oxidation of organic compounds. This was accomplished by flowing a known mixture of heated humid air with the organic vapor through an annular photoreactor. The pre-shrunk silica fiber mat coated with a titania film was supported with a stainless steel mesh. The coated film area that was irradiated was about 243 $cm^2$ for all the experiments. The light source was a 450 W medium pressure, mercury vapor, quartz UV lamp (Hanovia) and was placed inside a quartz cooling jacket that was immersed in the vapor phase reactor. The intensity of the UV light was measured using a photometer (International Light, Model IL 1400)

Liquid organic feed (HPLC grade from Aldrich) was pumped using a metering pump at a rate of 0.167 ml/min. The organic feed was heated and vaporized 1 before it was fed to the static mixer 2. Mass flow controllers were used to set the desired flows of air and supplementary oxygen at the rates of 1.5 and 0.5 l/min, respectively. Gases were heated before flowing to the static mixer. All the gases and the organic vapors were premixed in the static mixer that was maintained at constant temperatue. The experimental conditions used are listed in Table 2.

The exit stream from the reactor flows through a series of separators and traps to capture and separate the products and the unreacted feed 4. The unreacted feedstock was recycled 5 and the products were separated from condensed moisture 6.

Two different flame coating strategies were adopted: impingement of a precursor aerosol onto the heated substrate (FIG. 2), and by-feed of precursor and fuel through the burner (FIG. 3). The operating conditions for the flame coating method is listed in Table 2, and the number of passes were controlled to vary the thickness of the resultant titania films. As high temperatures were used during the applications of the coating, no additional steps were necessary and well adhered films were readily obtained in a single step.

Photoexcitation of immobilized semiconductor surfaces provides an environment wherein light induced redox reaction can take place, resulting in the selective oxidation or complete degradation of an organic substrate. To eliminate this problem the reactions were performed in a gas-phase photoreactor by flowing a known mixture of heated humid air with the organic vapor through an annular reactor. What makes this invention unique is the use of nanostructured semiconductor catalyst at optimized process conditions making it possible to achieve sufficiently high conversions and selectivities, and little or no detectable overoxidation. Results obtained from a gas phase reactor at 150° C., and with contact time of 8 sec are shown in Table 3.

TABLE 3

Summary of Results of Partial Oxidation of Hydrocarbon Using Photocatalysis

| Substrate | Conversion (%) | Products | Selectivity |
| --- | --- | --- | --- |
| Toluene | 6 to 12 | Benzyl Alcohol Benzaldehyde | 96–98% benzaldehyde |
| Cyclohexane | 2 to 6 | Cyclohexanol Cyclohexanone | 65–84% cyclohexanone |
| Methylcylohexane | 2 to 5 | Methylcyclohexanol (2,3,4) methylcyclohexanone (2,3,4) | 86–89% Methyl-cyclohexanone |
| Hexane | 2 to 4 | hexyl alcohol 2 and 3 - hexanols 2 and 3 - hexanons | 80% hexanone |
| Pentane | 1 to 2 | 1-, 2-, and 3 pentanols 1-, 2-, and 3 pentanones | 80% pentanone |
| Butane | 1 to 2 | Butanol, butanone | 75% ketone |
| Ethane | 0.5 to 1 | Ethanol, acetaldehyde | 89% ethanol |
| Methane | less than 1 | Methanol | 98% methanol |

The high selectivity obtained for toluene-to-benzaldehyde oxidation by $O_2$ without overoxidation or other side reactions is remarkable. The selectivity and efficiency with which the photoreactor operates were influenced by the oxygen concentration, the light illumination, the properties of the photocatalytic coating, and the conditions within the fluid phase affecting contact of the substrate to the $TiO_2$ surface. Current industrial process for toluene oxidation lacks this selectivity, mainly because of overoxidation to benzoic acid. Therefore, conversions have to be kept at lower percentages. The same is true for many other hydrocarbon substrates. The conventional method for the vapor-phase oxidation of cyclohexane using a nickel or boric acid catalysis also gives low conversions per pass (usually below 5%) in order for the yield of cyclohexane feedstock to reach 70+5[20]. The main obstacle in the improvement of the selectivity at high alkane conversion is overoxidation of the alcohol and ketone products. Using photocatalytic oxidation of cyclohexane it was possible to obtain up to 8% conversion perpass, better selectivities for ketones (up to 79%), with little side reaction or over-oxidations.

EXAMPLE 2

Different methods of preparing the photocatalyst (dip coating using titanium isopropoxide, commercially available process, sol-gel process and flame aerosol process) were used to deposit the titanium dioxide films (Table 4). Comparing the different catalyst preparation and coating method assists in proving the effectiveness of flame aerosol method. In all cases except Case 2, the crystal structure of the deposited titanium dioxide was primarily anatase. The flame coated process resulted in more open structures, which allows the penetration of UV light. Flame coating required the smallest mass of titanium dioxide to coat the surface and the smallest primary particle size as determined by transmission electron microscopy.

Two five-hour reaction cycles were used for testing six different films reactors (Table 4). The conversion, yield, reaction selectivity and activity are shown for the different systems. Conversions vary from 1.1 to 8.65 and yield exceeded 96%. The conventional vapor phase oxidation of cyclohexane using boric or nickel results in conversion 5% or less and the yield of about 70%. The selectivity of ketone formation varied from 59.7% to 91.7% for the different coatings. The flame coating (Case 6) resulted in the best performance with high conversion per unit mass of catalyst, yield and selectivity to ketone formation.

EXAMPLE 4

To examine the effect of coking on the catalyst surface, a second five hour testing cycle was used. The activity decreased for most of the films, and a visual browning of the catalyst surface was observed. A similar browning of $TiO_2$ film was observed by others for the gas phase oxidation of benzene using dry air. The degree of browning (or coking) was greatest for the dip coated films (Case 1 and 2), lesser for the sol-gel films (Case 3) and particularly absent for the flame aerosol coated films (Cases 4, 5 and 6). The minimal coking of the flame aerosol coated films could be due to the presence of solid primary particles (high density, with minimal internal porosity) and the high specific surface areas resulting in quicker desorption of the products (low retentivity on the surface) preventing the formation of higher molecular weight compounds on the surface.

The flame aerosol coating method enabled the formation of high surface area aggregates with minimal pore area coatings that were much more active the $TiO_2$ prepared by other methods. This coating did not appear to create interparticle diffusion control and exhibits no coking or deactivation.

TABLE 4

Conversion of Cyclohexane, Yield of Alcohol-Ketone (Ak) Formed, the Selectivity for Ketone Formation, and activity of coating

| Case | Coating Method | Run Cycle | Mass of $TiO_2$ per Unit area (mg/cm$^2$) | Conversion of Cyclohexane | Yield of AK (%) | Selectivity for Ketone | Activity ($\mu$mol/g min) |
|---|---|---|---|---|---|---|---|
| 1 | Dip-coating (TTIP precursor) | 1 | 9.6 | 8.62 | 98.6 | 91.7 | 0.013 |
|   |   | 2 |   | 7.36 | 98.9 | 72.6 | 0.013 |
| 2 | Dip-coating (particle precursor) | 1 | 2.5 | 8.1 | 96.5 | 74.1 | 0.273 |
|   |   | 2 |   | 6.2 | 98.8 | 59.7 | 0.181 |
| 3 | Sol-gel | 1 | 1.44 | 1.29 | 98.3 | 73.1 | 0.050 |
|   |   | 2 |   | 0.64 | 99.2 | 68.6 | 0.025 |
| 4 | Flame A | 1 | 0.78 | 2.69 | 98.2 | 74.4 | 0.396 |
|   |   | 2 |   | 2.71 | 97.1 | 72.2 | 0.395 |
| 5 | Flame B | 1 | 0.37 | 1.11 | 96.5 | 74.4 | 0.490 |
|   |   | 2 |   | 1.17 | 97.1 | 73.1 | 0.362 |
| 6 | Flame C | 1 | 0.49 | 3.9 | 98.0 | 83.0 | 0.964 |
|   |   | 2 |   | 1.9 | 96.5 | 79.2 | 0.446 |

EXAMPLE 3

To better establish the role of catalyst the activity of the catalyst was reported as the amount of product formed per gram of catalyst per time. This definition of catalyst is similar to the turnover number per unit mass of catalyst per unit time, and provides a basis for an overall comparison of the different coatings. The activity ranged from 0.013 $\mu$mole/(gm.min) for the dip coating method (Case 1) to a high value of 0.969 $\mu$mole/(gm.min) for the flame aerosol method (Case 6) (Table 2).

Figure 4:
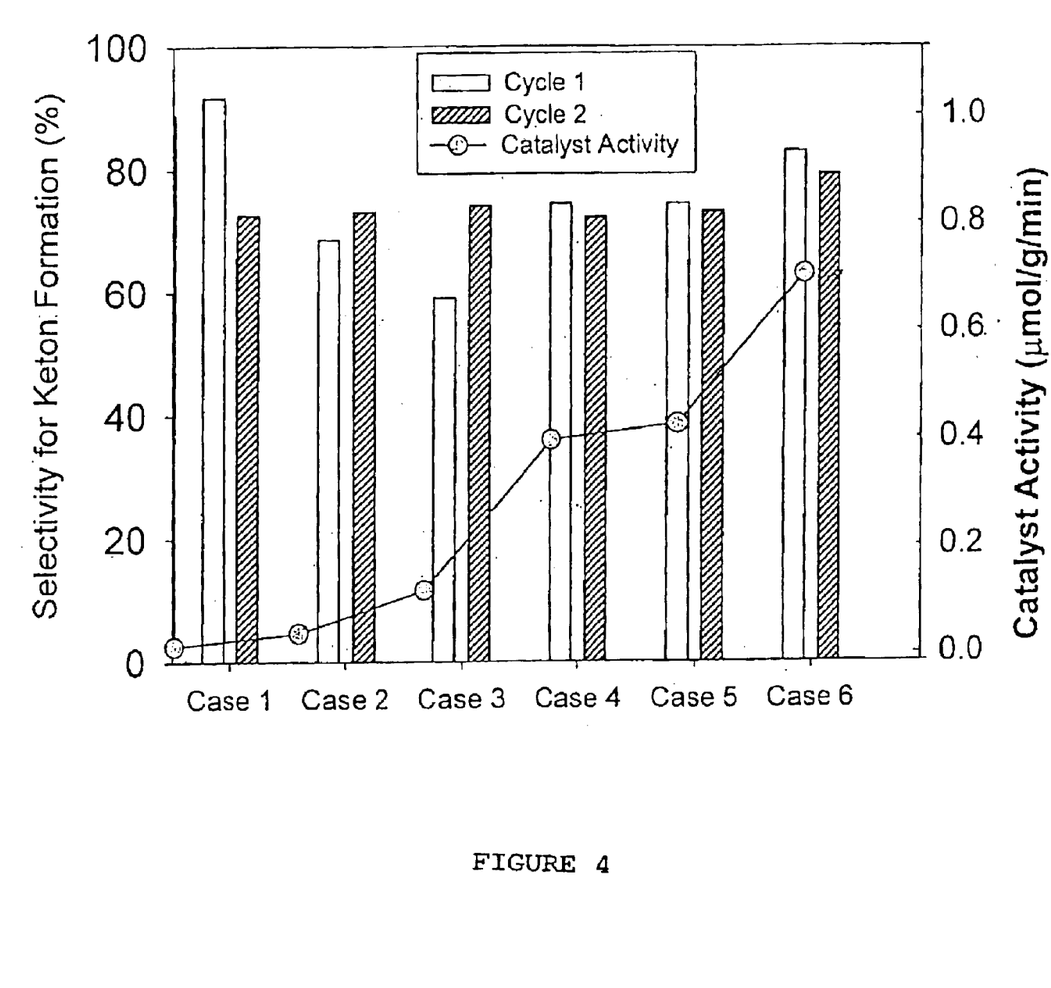
FIG. 4 is a graphical illustration showing selectivity of ketone formation and conversion per mass of titanium dioxide for different coating methods.
Figure 5:
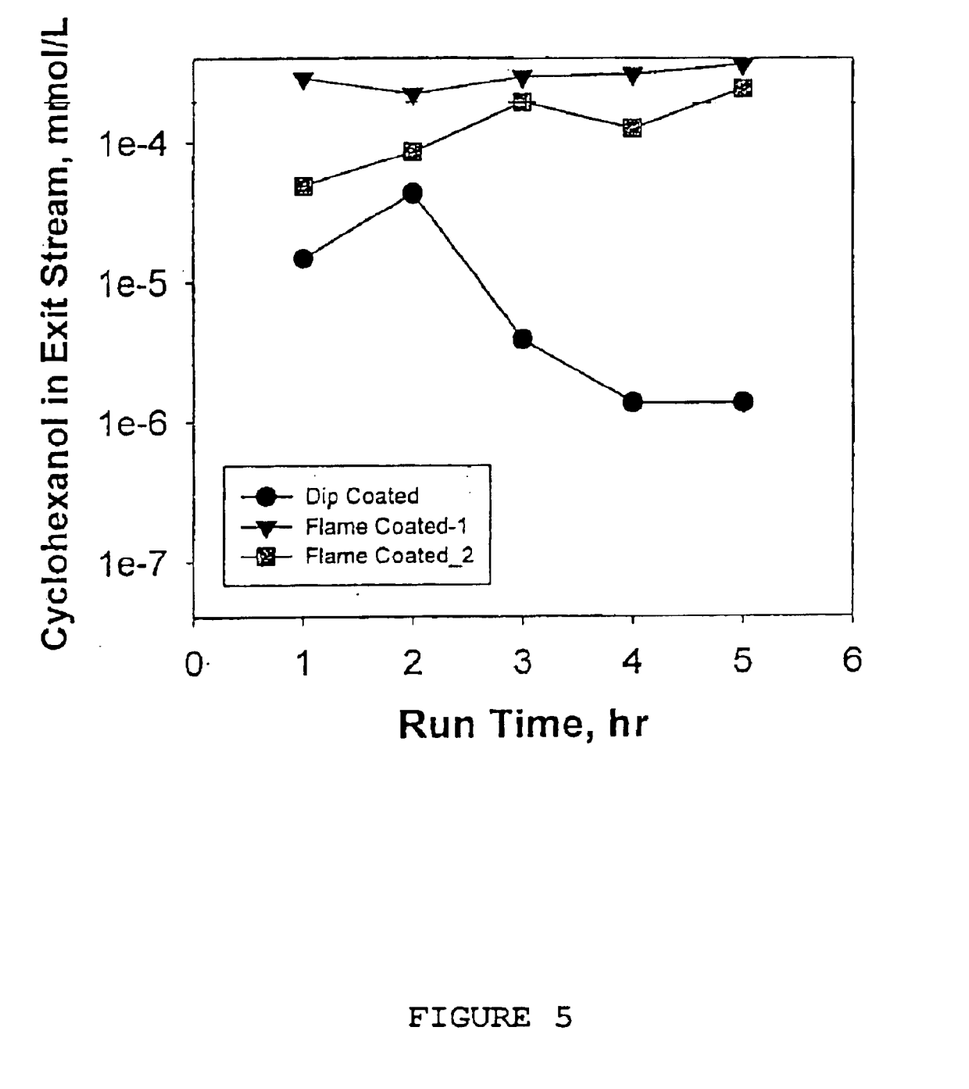
FIG. 5 is a graphical illustration showing cyclohexanol concentrations, a product of cyclohexane gas phase oxidation, in the exit stream from a photoreactor with catalyst prepared using different coating methods.
Figure 6:
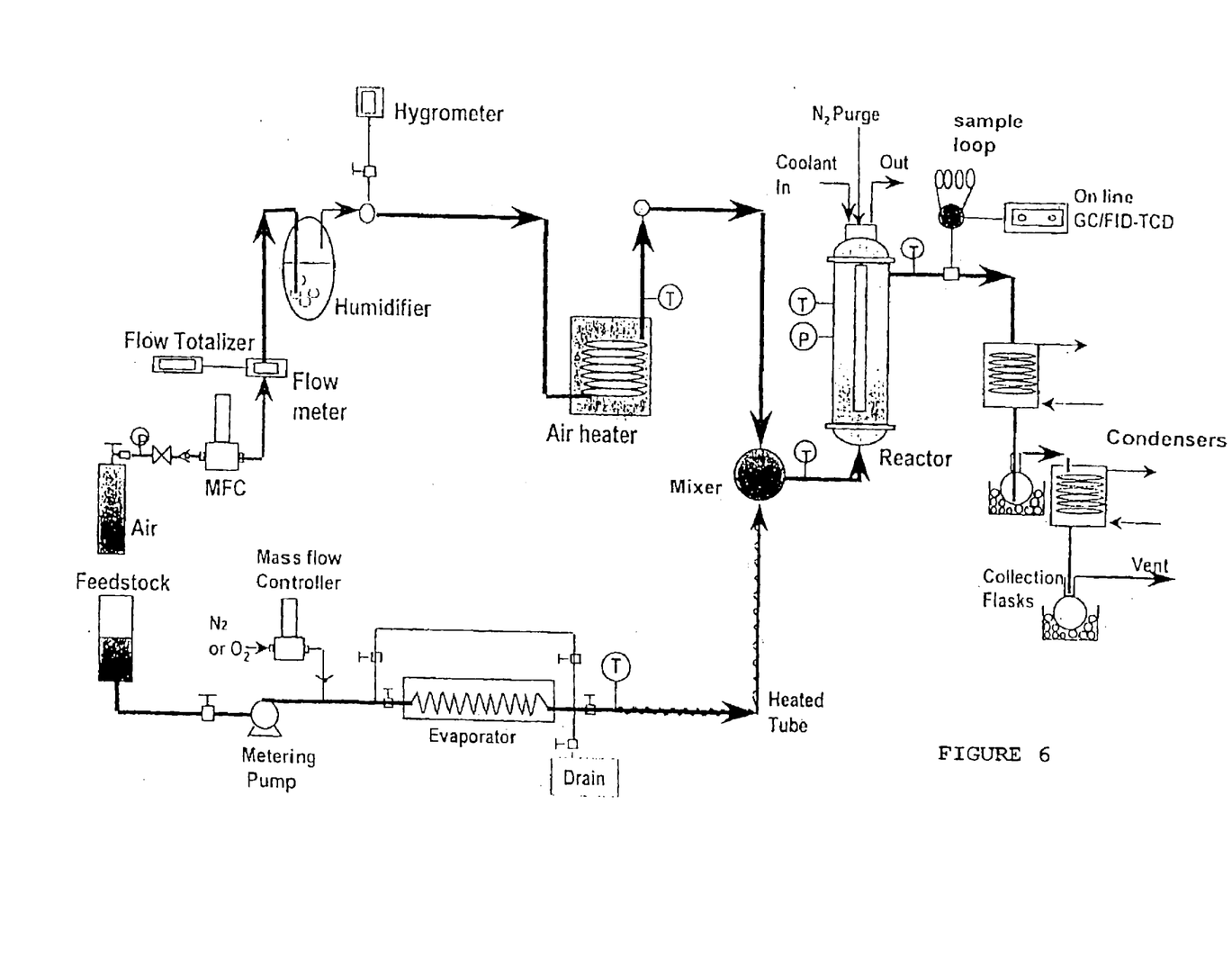
FIG. 6 shows a process flow diagram for a continuous reaction system for performing gas phase photo-activated catalytic oxidation of organic compounds.

The flame aerosol coating showed higher effectiveness due to the open structure of the coating and the nanometer size primary particles that creates more electron-hole pairs for the redox reactions. Furthermore, the high specific surface areas resulted in quick desorption of the products, and this minimized coking on the catalyst surface. FIG. 4 illustrates the comparative performance of the thin film reactors prepared by the different coating methodologies. The flame aerosol method resulted in the coatings that are most effective at partial oxidation.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood the phraseology or terminology employed herein is for the purpose of description and not of limitation.

What is claimed is:

1. A photocatalyst for partial oxidation reactions comprising a semiconductor that has been deposited from a coating precursor onto a substrate by flame aerosol deposition to form a nanostructured film.

2. The photocatalyst according to claim 1 wherein the semiconductor is titanium dioxide.

3. The photocatalyst according to claim 2 wherein the titanium dioxide is in a form selected from the group consisting of anatase, rutile, and mixtures thereof.

4. The photocatalyst according to claim 1 wherein the coating precursor is selected from the group consisting of isopropoxides, nitrates, carbonyls, and halides of the cation forming the photocatalyst.

5. The photocatalyst according to claim 4 wherein the coating precursor is selected from the group consisting of titanium isopropoxide, ferric nitrate, titanium tetrachloride, tin chloride, and silicon tetrachloride.

6. The photocatalyst according to claim 1 wherein the substrate is selected from the group consisting of silica fibers, silica, quartz, stainless steel, steel, and aluminum.

7. The photocatalyst according to claim 1 wherein the photocatalyst is in the form of a nanostructured film.

8. The photocatalyst according to claim 7 wherein the nanostructured film is from about 50 nm to about 1.5 micron in thickness.

9. The photocatalyst according to claim 8 wherein the nanostructured film is from about 50 nm to about 0.8 micron in thickness.

10. The photocatalyst according to claim 1 wherein the semiconductor is in particles of average diameter of about 150 nm to about 400 nm.

* * * * *